United States Patent
Fauser et al.

(10) Patent No.: US 8,569,274 B2
(45) Date of Patent: Oct. 29, 2013

(54) PROGESTERONE ANTAGONIST AND SELECTIVE PROGESTERONE MODULATOR IN THE TREATMENT OF EXCESSIVE UTERINE BLEEDING

(75) Inventors: Bartholomeus C. J. M. Fauser, Rotterdam (NL); Ernest Loumaye, Plan-les-Ouates/Geneva (CH)

(73) Assignee: Preglem S.A., Geneva (CH)

( * ) Notice: Subject to any disclaimer, the term of this patent is extended or adjusted under 35 U.S.C. 154(b) by 816 days.

(21) Appl. No.: 12/596,624

(22) PCT Filed: Apr. 18, 2008

(86) PCT No.: PCT/IB2008/000945
§ 371 (c)(1),
(2), (4) Date: Mar. 29, 2010

(87) PCT Pub. No.: WO2008/129396
PCT Pub. Date: Oct. 30, 2008

(65) Prior Publication Data
US 2010/0190758 A1    Jul. 29, 2010

Related U.S. Application Data

(60) Provisional application No. 60/907,875, filed on Apr. 20, 2007.

(51) Int. Cl.
*A61K 31/56* (2006.01)
(52) U.S. Cl.
USPC .......................................... 514/172; 514/182
(58) Field of Classification Search
USPC ................................................. 514/171, 182
See application file for complete search history.

(56) References Cited

U.S. PATENT DOCUMENTS

| | | |
|---|---|---|
| 6,451,780 B1 | 9/2002 | Chwalsz et al. |
| 7,183,309 B2 | 2/2007 | Jiang et al. |

FOREIGN PATENT DOCUMENTS

| | | |
|---|---|---|
| WO | WO 96/23503 A1 | 8/1996 |
| WO | WO 2006/010097 A2 | 1/2006 |

OTHER PUBLICATIONS

Attardi, B.J., et al., "CDB-4124 and its putative monodemethylated metabolite, CDB-4453, are potent antiprogestins with reduced antiglucocorticoid activity: in vitro comparison to mifepristone and CDB-2914," Mol. Cell. Endocrinol. 188 (12): 111-23, Elsevier Science Ireland Ltd. (Feb. 2002).

Chwalisz, K., et al., "Selective progesterone receptor modulator development and use in the treatment of leiomyomata and endometriosis," Endocr. Rev. 26(3): 423-38, Endocrine Society, United States (May 2005; Epub Apr. 2005).

Erikci, A.A., et al., "Recombinant activated factor VII for severe uterine bleeding after chemotherapy in a woman with acute myeloid leukemia," Blood Coagul. & Fibrinolysis 17(4): 323-324, Lippincott Williams & Wilkins (Jun. 2006).

Miller, J. & Holman, J.R., "Abnormal uterine bleeding: A primary care primer," Consultant 45(6): 638-645, UBM Medica (May 2005).

Munro, M.G., "Abnormal uterine bleeding in the reproductive years. Part II—medical management," J. Am. Assoc. Gynecol. Laparosc. 7(1): 17-35, Journal of American Association of Gynecologic Laparoscopists, American Association of Gynecologic Laparoscopists (Feb. 2000).

Munro, M.G., "Medical management of abnormal uterine bleeding," Obstet. Gynecol. Clin. North Am. 27 (2): 287-304, Elsevier Science. Jun. 2000.

Passaro, M.D., et al., "Luteal phase dose-response relationships of the antiprogestin CDB-2914 in normally cycling women," Hum Reprod. 18(9): 1820-7, Oxford University Press, England (Sep. 2003).

Smith, C.L. & O'Malley, B.W., "Coregulator function: a key to understanding tissue specificity of selective receptor modulators," Endocr. Rev. 25(1): 45-71, The Endocrine Society, United States (Feb. 2004).

Spitz, I.M., "Progesterone receptor antagonists," Curr. Opin. Investig. Drugs. 7(10) 882-90, BioMed Central Ltd. (Oct. 2006).

Bates, J.S., et al., "Managment of Menorrhagia Associated with Chemotheraphy-Induced Thrombocytopenia in Women With Hematologic Malignancy," *Pharmacotherapy* 31(11):1092-1110, Wiley-Blackwell, United States (Nov. 2011).

Donnez, J., et al., "Ulipristal Acetate versus Placebo for Fibroid Treatment before Surgery," *N. Engl. J. Med.* 366(5):409-420, Massachusetts Medical Society, United States (Feb. 2012).

Donnez, J., et al., "Ulipristal Acetate versus Leuprolide Acetate for Uterine Fibroids," *N. Engl. J. Med.* 366(5):421-432, Massachusetts Medical Society, United States (Feb. 2012).

Lukes, A.S., et al., "Tranexamic Acid Treatment for Heavy Menstrual Bleeding: A Randomized Controlled Trial," *Obstet. Gynecol.* 116(4):865-875, Lippincott Williams & Wilkins, United States (Oct. 2010).

Meirow, D., et al., "Prevention of Severe Menorrhagia in Oncology Patients with Treatment-Induced Thrombocytopenia by Luteinizing Hormone-Releasing Hormone Agonist and Depo-Medroxyprogesterone Acetate," *Cancer* 107(7):1634-1641, Wiley, United States (Aug. 2006).

*Primary Examiner* — San-Ming Hui
(74) *Attorney, Agent, or Firm* — Sterne, Kessler, Goldstein & Fox P.L.L.C.

(57) ABSTRACT

Progesterone antagonists and SPRM are useful to prepare a medication for the treatment or the prophylaxis of excessive uterine bleeding in women with spontaneous or iatrogenic coagulation disorders such as thrombopenia, coagulation factor deficiency or anti-coagulant therapy. Treatment will last from 1 day to 180 days.

14 Claims, No Drawings

PROGESTERONE ANTAGONIST AND SELECTIVE PROGESTERONE MODULATOR IN THE TREATMENT OF EXCESSIVE UTERINE BLEEDING

CROSS-REFERENCE TO RELATED APPLICATIONS

This application is a National Stage of International Application No. PCT/IB2008/000945, filed on Apr. 18, 2008, which claims the benefit of U.S. Provisional Application No. 60/907,875, filed on Apr. 20, 2007, the entire contents of which are herein incorporated by reference.

FIELD OF THE INVENTION

Progesterone antagonists and SPRM are useful to prepare a medication for the treatment or the prophylaxis of excessive uterine bleeding in women with spontaneous or iatrogenic coagulation disorders such as thrombopenia, coagulation factor deficiency or anti-coagulant therapy. Treatment will last from 1 day to 180 days.

BACKGROUND OF THE INVENTION

Uterine bleeding when abnormal can lead to significant anemia and can even be life-threatening. Anatomical causes such as fibroid, polyps, endometrium carcinoma or endometrium hyperplasia resulting from prolonged un-opposed oestrogens deserve specific treatments which are progestins, or surgery like curettage, endoscopic resection or hysterectomy.

Dysfunctional uterine bleeding disorders (dysfunctional or abnormal uterine bleeding, metrorrhagia and menorrhagia, hypermenorrhea) are forms of pathological bleeding that are not attributable to organic changes in the uterus (such as, e.g., endometrial carcinoma, myomas, polyps, etc.), systemic coagulation disorders, or a pathological pregnancy (e.g., ectopic pregnancy, impending abortion) [American College of Obstetricians and Gynecologists, 1982]. Such disorders are most frequent after puberty or before menopause. Treatment is medical using oestrogens and progestins. If not successful and patient does not wish to preserve fertility, hysterectomy or endometrial ablation may be performed.

Another group of patients in whom controlling abnormal uterine bleeding is a clinical challenge is patients with severe coagulation disorders. These coagulation disorders results from (i) pro-coagulant protein deficiency due to genetic defect (e.g. hemophilia or von Willebrand disease) or functional deficiency (e.g. hepatic function impairment), (2) thrombocytopenia caused by decreased bone marrow production of megakaryocytes (e.g. leukemia), splenic sequestration or increased destruction of platelets (e.g. disseminated intravascular coagulation), (3) bone marrow aplasia resulting from oncological treatments such as chemotherapy and total body irradiation, and (4) inadequate anticoagulation treatment.

These conditions are difficult to manage because bleeding can be very severe and these patients often have impaired general condition with for example immunodeficiency in leukemia or bone marrow aplasia. Specific treatment like platelet transfusion, blood transfusion and coagulation factor administration are used to attempt controlling bleeding. Oestrogens and progestins are also used with relative success and possible side effects. Inducing reversible castration by sustained administration of a GnRH agonist has also been reported to be useful in some cases for preventing severe bleeding prior to chemotherapy. Surgical intervention in these patients with altered general condition and immuno-deficiency are at risk.

Being able to medically treat patients with acute conditions such as acute phase of leukemia or treat or prevent uterine bleeding during the acute phase of iatrogenic bone marrow aplasia or treat or prevent uterine bleeding in patients under anticoagulation therapy for conditions banning the use of oestrogens and/or progestins (e.g. thrombo-embolic conditions), will meet a very significant medical need.

SUMMARY OF THE INVENTION

The present invention concerns a method of treating and/or preventing excessive uterine bleeding resulting from a coagulation disorder consisting essentially in administering a therapeutically effective amount of a progesterone antagonist, a SPRM, or an active metabolite thereof, to a woman in need thereof.

A further object of the present invention is to provide the use of a progesterone antagonist, a SPRM, or an active metabolite thereof for the preparation of a medicament in the treatment and/or prevention of excessive uterine bleeding resulting from a coagulation disorder, in a woman in need thereof.

The invention also contemplates kit for treating and/or preventing excessive uterine bleeding resulting from a coagulation disorder comprising a therapeutically effective amount of a progesterone antagonist, a SPRM, or an active metabolite thereof optionally with reagents and/or instructions for use.

DETAILED DESCRIPTION OF THE INVENTION

The present invention relates to a method of treating and/or preventing excessive uterine bleeding resulting from a coagulation disorder consisting essentially in administering a therapeutically effective amount of a progesterone antagonist, a SPRM, or an active metabolite thereof, to a woman in need thereof.

As used herein, "a" or "an" means "at least one" or "one or more."

As used herein, the term "comprise" is generally used in the sense of include, that is to say permitting the presence of one or more features or components.

A "therapeutically effective amount" is an amount effective to ameliorate, treat or prevent the symptoms, diseases or disorders in a mammal, or prolong the survival of the subject being treated.

The terms "treating and/or preventing" refer to both therapeutic treatment and prophylactic or preventative measures. Those women in need of treatment include those already suffering from excessive uterine bleeding resulting from a coagulation disorder as well as those in which said disorder is to be prevented. Hence, the subject to be treated herein may have been diagnosed as having said disorder or may be predisposed or susceptible to said disorder.

The term "SPRM" stands for selective progesterone receptor modulator and represents a class of progesterone receptor ligands that exerts clinically relevant tissue-selective progesterone agonist, antagonist, or partial (mixed) agonist/antagonist effects on various progesterone target tissues in an in-vivo situation depending on the biological action studied (Smith C L and O'Malley B W, 2004, Coregulator function: a key to understanding tissue specificity of selective receptor modulators in *Endocr Rev* 25:45-71.)

As used herein, "a progesterone receptor antagonist" or "a progesterone antagonist" refers to a compound or agent that inhibits the activity of the progesterone receptor.

"Administering", as it applies in the present invention, refers to contact of a therapeutically effective amount of a progesterone antagonist, a SPRM, or an active metabolite thereof, to the subject, preferably a woman.

As used herein "excessive uterine bleeding resulting from a coagulation disorder" refers to a category of uterine bleeding disorders different from dysfunctional uterine bleeding disorders. The endometrium of patients suffering from excessive uterine bleeding resulting from a coagulation disorder is healthy. Additionally, these patients do no systematically respond to standard therapy such as progestin treatment, on the contrary to patients suffering from bleedings resulting from dysfunctional uterine bleeding disorders. That is probably the reason why patients suffering from excessive uterine bleeding resulting have been excluded from SPRM treatment described by Chwalsz Christopher et al., in U.S. Pat. No. 6,451,780 B1, indicating that for experts other therapeutic approaches as those currently available are be needed.

Surprisingly, Applicants have shown that it is possible to treat and/or prevent excessive uterine bleeding resulting from a coagulation disorder by administering a therapeutically effective amount of a progesterone antagonist, a SPRM or an active metabolite thereof to a woman suffering form these disorders.

This method of treating and/or preventing excessive uterine bleeding resulting from a coagulation disorder, controls uterine bleeding during a period of up to 6 months or is initiated prior to inducing thrombopenia/aplasia for preventing severe uterine bleeding and is continued throughout symptoms period.

Progesterone antagonist and SPRM have been shown to be very well tolerated. PA/SPRM administration is not associated with the metabolic adverse effects observed with oestrogens and progestins, nor with the castration symptoms induced by GnRH agonist therapy.

Progesterone antagonists and SPRM have been shown to stop uterine bleeding within a few days in organic conditions such as uterus fibroid most likely through a direct endometrium effect. Reference has been made to the use of SPRM in dysfunctional uterine bleeding although no data have been published so far. All these conditions are attributable to local disruption of the endometrium integrity.

Surprisingly enough, it has been found that progesterone antagonist/SPRM are able to reduce and stop uterine bleeding in patients with normal endometrium but altered coagulation.

The progesterone antagonist or SPRM that are consider for this invention are selected form the group comprising, but not limited to, CDB2914, mifepristone, asoprisnil, proellex, onapristone, org33628, tanaproget, tanaproget-combo, WAY 166989, NSP 989, NSP-combo, and 11[beta]-benzaldoxime substituted SPRMs such as, foe example, 11[beta]-((4-N,N-Dimethylamino)-phenyl-17[beta]-hydroxy-17[alpha]-propinyl-4,9(10)-estradien-3-one-(RU-38486), 11[beta]-((4-N,N-dimethylamino)-phenyl)-17[beta]-hydroxy-18-methyl-17[alpha]-propinyl-4,9(10)-estradien-3-one, 11[beta]-((4-N,N-dimethylamino)-phenyl)-17[alpha][beta]-hydroxy-17a[alpha]-propinyl-D-homo-4,9(10),16-estratien-3-one, 11[beta]-p-methoxyphenyl-17[beta]-hydroxy-17[alpha]-ethinyl-4,9(10)-estradien-3-one, 11[beta]-(4-acetylphenyl)-17[beta]-hydroxy-17[alpha]-(prop-1-inyl)-4,9(10)estradien-3-one, 11[beta]-(4-dimethylaminophenyl)-17[alpha]-hydroxy-17[beta]-(3-hydroxy-propyl)-13[alpha]-methyl-4,9-gonadien-3-one, (Z)-11[beta]-[4-(dimethylamino)phenyl]-17[beta]-hydroxy-17[alpha]-(3-hydroxy-1-propenyl)-estr-4-en-3-one-5,11[beta], 19-(4-acetylphenyl)-17[beta]-hydroxy-17[alpha]-(3-hydroxyprop-1-(Z)-enyl)-4,9(10)-estradien-3-one, 11[beta], 19-(4-cyanophenyl)-17[beta]-hydroxy-17[alpha]-(3-hydroxyprop-1-(Z)-enyl)-4-androsten-3-one or 11[beta], 19-(4-(3-pyridinyl)-o-phenylene)-17[beta]-hydroxy-17[alpha]-(3-hydroxyprop-1-(Z)-enyl)-4-androsten-3-one, 17[alpha]-acetoxy-21-methoxy-11β-[4-N,N-dimethylaminophenyl]-19-norpregna-4,9-diene-3,20-dione (CDB-4124, Proellex®), It is known that progesterone receptor existed as two isoforms, full-length progesterone receptor isoform (PR-B) and its shorter counterpart (PR-A). Recently, extensive studies have been implemented on the progesterone receptor knockout mouse (PRKO, lacking both the A- and B-forms of the receptors). These findings provided great challenge for synthetic chemists to construct not only selective progesterone receptor modulator (SPRM), but also PR-A or PR-B selective progesterone receptor modulator.

Accordingly, also encompassed in the present invention is the use of PR-A or PR-B selective progesterone receptor modulator such as the indole derivatives described in U.S. Pat. No. 7,183,309 (JIANG WEIQIN et al.) which disclosure is incorporated herein as a whole.

The method of the invention also considers the administration of a therapeutically effective amount of an active metabolite of progesterone antagonist or of an active metabolite of a SPRM. An "active metabolite" is a product produced through metabolism in the body of a specified compound or salt thereof and which exhibits the same biological activity as the specified compound. Active metabolites of a progesterone antagonist or of a SPRM may be identified using routine techniques known in the art and their activities determined using tests such as those described herein. Such metabolites may result for example from the oxidation, reduction, hydrolysis, amidation, deamidation, esterification, deesterification, enzymatic cleavage, and the like, of the administered progesterone antagonist or SPRM. Accordingly, the invention includes active metabolites of a progesterone antagonist or a SPRM, including compounds produced by a process comprising contacting a compound of this invention with a mammal for a period of time sufficient to yield a metabolic product thereof. Such metabolite may also be produced in vitro by oxidation, reduction, hydrolysis, amidation, deamidation, esterification, deesterification, or enzymatic cleavage of the corresponding progesterone antagonist or SPRM.

Examples of active metabolites of progesterone antagonists or SPRM are shown in the following table 1:

| Progesterone antagonist/SPRM | Active Metabolite |
|---|---|
| asoprisnil | J912 |
|  | J956 |
| CDB-4124 | CDB-4453 |
| CDB-2914 | CBD-3877, CDB-3963, CDB-3236 and CDB-4183 |

According to this invention, the progesterone antagonist, the SPRM or an active metabolite thereof will be administered, preferably daily, by oral route for a period of 1 to 180 days. During this treatment period, the administration can be stopped if condition leading to uterine bleeding has been corrected e.g. correction of thrombocytopenia or stopping anticoagulation treatment.

Alternatively, the progesterone antagonist, the SPRM or an active metabolite thereof will be administered, every other day, once a week or once every month, preferably, as a one-time administration.

Usually, the progesterone antagonist, the SPRM or an active metabolite thereof will be administered during bleeding peaks or during menstruation in an amount sufficient to treat and/or prevent excessive uterine bleeding which results from a coagulation disorder.

Usually, the progesterone antagonist, the SPRM or an active metabolite thereof is administered at a daily dose between 0.1 to 1000 mg. However, the appropriate dosage will depend on the progesterone antagonist, the SPRM, or the active metabolite thereof. In case the SPRM is CDB-2914, it will be administered at a daily dose between 1 to 15 mg, most preferably between 5 to 10 mg and even more preferably at 10 mg (per day).

Progesterone antagonist, the SPRM or an active metabolite thereof for use in the method as described herein, are usually in the form of a pharmaceutical composition that may contain one or more pharmaceutically acceptable carriers, such as excipients, carriers and/or auxiliaries which facilitate processing of the active compounds into preparation which can be used pharmaceutically.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as TWEEN®, PLURONICS® or polyethylene glycol (PEG).

The form of administration of the pharmaceutical composition may be systemic or topical. For example, administration of such a composition may be various parenteral routes such as vaginal, rectal, subcutaneous, intravenous, intradermal, intramuscular, intraperitoneal, intra-uterine, intranasal, transdermal, buccal routes or via an implanted device, and may also be delivered by peristaltic means. Preferably, the form of administration of the pharmaceutical composition comprising the progesterone antagonist, the SPRM or an active metabolite thereof is by oral administration, followed by the vaginal route.

One variation of the present invention also foresees a pharmaceutical composition suitable for delayed and controlled release of the Progesterone antagonists and SPRM as defined in the present invention. The Progesterone antagonists and SPRM, for example, may be incorporated in a matrix of biocompatible polymer allowing delayed and controlled release. All biocompatible polymers, well known by those skilled in the art are potential candidate to be used in this invention. Vaginal rings or intra-uterine devices are also contemplated options.

Sustained-release preparations may be prepared. Suitable examples of sustained-release preparations include semi permeable matrices of solid hydrophobic polymers containing the progesterone antagonist or SPRM, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma] ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished for example by filtration through sterile filtration membranes.

It is understood that the suitable dosage of the progesterone antagonist, the SPRM or an active metabolite thereof of the present invention will be dependent upon the age, health, and weight of the woman in need thereof, kind of concurrent treatment, if any and the nature of the effect desired.

The appropriate dosage form will depend on the disease, the progesterone antagonist, the SPRM, or an active metabolite thereof and the mode of administration; possibilities include tablets, capsules, lozenges, pills, dental pastes, suppositories, inhalants, solutions, ointments, parenteral depots, vaginal rings and intra-uterine delivery systems.

In cases where the progesterone antagonist, the SPRM, or an active metabolite thereof is included in a solution, the formulation may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, among others.

Useful intranasal formulations of progesterone antagonist, the SPRM, or an active metabolite thereof may contain a stabilizers and a surfactants. Among the pharmaceutically acceptable surfactants are polyoxyethylene castor oil derivatives, such as polyoxyethylene-glycerol-triricinoleate, also known as polyoxyl 35 caster oil (CREMOPHOR EL), or poloxyl 40 hydrogenated castor oil (CREMOPHOR RH40) both available from BASF Corp.; mono-fatty acid esters of polyoxyethylene (20) sorbitan, such as polyoxyethylene (20) sorbitan monolaurate (TWEEN 80), polyoxyethylene monostearate (TWEEN 60), polyoxyethylene (20) sorbitan monopalmitate (TWEEN 40), or polyoxyethylene 20 sorbitan monolaurate (TWEEN 20) (all available from ICI Surfactants of Wilmington, Del.); polyglyceryl esters, such as polyglyceryl oleate; and polyoxyethylated kernel oil (LABRAFIL, available from Gattefosse Corp.). Preferably, the surfactant will be between about 0.01% and 10% by weight of the pharmaceutical composition. Among the pharmaceutically useful stabilizers are antioxidants such as sodium sulfite, sodium metabisulfite, sodium thiosulfate, sodium formaldehyde sulfoxylate, sulfur dioxide, ascorbic acid, isoascorbic acid, thioglycerol, thioglycolic acid, cysteine hydrochloride, acetyl cysteine, ascorbyl palmitate, hydroquinone, propyl gallate, nordihydroguaiaretic acid, butylated hydroxytoluene, butylated hydroxyanisole, alpha-tocopherol and lecithin. Preferably, the stabilizer will be between about 0.01% and 5% by weight of the pharmaceutical composition.

Suspensions may also include chelating agents such as ethylene diamine tetraacetic acid, its derivatives and salts thereof, dihydroxyethyl glycine, citric acid and tartaric acid among others. Additionally, proper fluidity of a suspension can be maintained, for example, by the use of coating materials such as lecithin, by the maintenance of the required particle size in the case of dispersions and by the use of surfactants, such as those previously mentioned. Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or (a) fillers or extenders such as starches, lactose, sucrose, glucose, mannitol and silicic acid; (b) binders such as carboxymethylcellulose, alginates, gelatin, polyvinylpyrrolidone, sucrose and acacia; (c) humectants such as glycerol; (d) disintegrating agents such as agar-agar, calcium carbonate, potato or tapioca starch, alginic acid, certain silicates and sodium carbonate; (e) solution retarding agents such as paraffin; (f) absorption accelerators such as quaternary ammonium compounds; (g) wetting agents such as cetyl alcohol and glycerol monostearate; (h) absorbents such as kaolin and bentonite clay; and (i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills and granules can be prepared with coatings and shells such as enteric coating and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

This invention also envisages the use of the progesterone antagonist, the SPRM, or an active metabolite thereof in a pharmaceutically acceptable salt form. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like. Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, pamoic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention. All such acid and base salts are intended to be pharmaceutically acceptable salts within the scope of the invention and all acid and base salts are considered equivalent to the free forms of the corresponding compounds for purposes of the invention.

Alternatively, or additionally, it will become apparent that the pharmaceutical composition may be administered alone or in combination with other treatments, therapeutics or agents, either simultaneously or sequentially dependent upon the condition to be treated. For example, the progesterone antagonist, the SPRM or an active metabolite thereof in the method of the invention may be administered in association with an oestrogen either simultaneously or sequentially. This association may allow, in certain conditions, to increase bleeding control while minimizing oestrogen exposure.

A further object of the present invention is to provide the use of a progesterone antagonist, a SPRM, or an active metabolite thereof for the preparation of a medicament in the treatment and/or prevention of excessive uterine bleeding resulting from a coagulation disorder, in a woman in need thereof.

The present invention also contemplates a kit for treating and/or preventing excessive uterine bleeding resulting from a coagulation disorder comprising the progesterone antagonist, the SPRM or an active metabolite, optionally with reagents and/or instructions for use.

Generally, the Kit comprises a container and a label or package insert on or associated with the container. Suitable containers include, for example, bottles, vials, syringes, etc. The containers may be formed from a variety of materials such as glass or plastic. The container holds the progesterone antagonist, the SPRM or an active metabolite of the invention which is effective for treating and/or preventing excessive uterine bleeding resulting from a coagulation disorder and may have a sterile access port (for example the container may be an intravenous solution bag or a vial having a stopper pierceable by a hypodermic injection needle or an aerosol spray device). The label or package insert indicates that the composition is used for treating the condition of the invention.

Alternatively, or additionally, the Kit may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1

A 19 year-old post-pubertal woman is consulting for fever, infections, uterine bleeding, petechia and dyspnea. Blood test identifies anemia (Hb 7.8 g/dL), normal leucocyte count (WBC 8657 cells/µL) and thrombocytopenia (platelets: 13.476 cells/mm$^3$). A bone marrow biopsy is performed which shows a hypercellular bone marrow, with a monomorphic infiltration of leukemic blasts and a marked reduction in normal bone marrow elements. A diagnosis of Acute Lymphotic Leukemia is confirmed.

The patient undergoes blood and platelet transfusion to correct for anemia and coagulation disorder. On the same day, she starts taking orally 10 mg/day of CDB-2914. Uterine bleeding quickly improved and 5 days following initiation of treatment, bleeding is stopped. On that day, Hb is 9.9 g/dL; WBC 6345 cells/µL; and platelet count is 42 000 cells/mm$^3$.

She continues taking orally 10 mg/day of CDB2914 for controlling abnormal uterine bleeding. Except for a few spotting, she remains in amenorrhea (absence of uterine bleeding) despite several episode of thrombopenia related to her conditions and chemotherapy cycles.

After 3 months, she achieves remission, Hb is 13.1 g/dL; leucocyte count is normal, platelet count is 176 000 cells/mm$^3$. Bone marrow biopsy confirmed normalization. CDB2914 treatment is stopped, and regular, normal menstrual bleeding are restored.

Example 2

A 31 year-old women is consulting for pneumonia. She reports a recent history of night sweats and weight loss. Chest X ray shows significant mediastinal adenopathies and a complete assessment for lymphoma is undertaken. The diagnosis is a stage III of Hodgkin disease. Her condition indicates chemotherapy (MOPP) and extended irradiation. The main risk of the proposed therapy is bone marrow suppression. This is life-threatening by exposing the patient to severe infection and septicemia, but it is also associated with severe thrombopenia and diffuse bleeding including uterine bleeding.

In order to prevent uterine bleeding, before initiating specific treatment for her Hodgkin disease, she is orally administered 10 mg/day of CDB-2914. Following initiation of chemotherapy and irradiation, severe bone marrow suppression is recorded and the patient is admitted in aseptic unit. Despite severe thrombopenia, the patient remains in amenorrhea. CBD2914 administration is maintained as long as coagulation parameters are not normalized.

In both cases, reduction of bleeding allowed reduction in platelet transfusion and total volume of blood transfused.

Example 3

A 42 year-old, moderate smoker women with a BMI at 32 is treated with anticoagulant therapy for an episode of pulmonary embolism resulting from a deep venous thrombosis in a leg. Despite effort to adapt her anticoagulation therapy, her menstruations are heavy (menorrhagia) and last for up to two weeks. Her Hb is at 9.2 gr/dL. Trans-vaginal ultrasound, endometrium biopsy and hysteroscopy do not reveal an underlying condition which may cause her menorraghia.

Her thrombo-embolic condition precludes any therapy with oestrogens or progestins. Given, the absence of negative metabolic and pro-thrombotic effect of SPRM, she is orally administered 25 mg/day of Proellex® (CDB-4124). Uterine bleeding stopped after a few days and the patient remain amenorrheic during the 12 weeks of anticoagulation therapy. Her Hb progressively returned to normal (>12 gd/dL).

After anticoagulation therapy is stopped, Proellex® is stopped and the patients resumed normal menstruations.

The invention claimed is:

1. A method of treating excessive uterine bleeding resulting from a coagulation disorder comprising administering a therapeutically effective amount of a progesterone antagonist, a selective progesterone receptor modulator (SPRM), or an active metabolite thereof, or a combination of two or more of said progesterone antagonists, SPRMs, or active metabolites, or a combination of two or more of said progesterone antagonists, SPRMs or active metabolites thereof, to a woman in need thereof, wherein
said progesterone antagonist or SPRM is selected from the group consisting of CDB-2914, mifepristone, asoprisnil, CDB-4124, onapristone, org33628, tanaproget, tanaproget-combo, 11 beta-((4-N,N-dimethylamino)-phenyl)-17 beta-hydroxy-18-methyl-17 alpha-propinyl-4,9(10)-estradien-3-one, 11 beta-((4-N,N-dimethylamino)-phenyl)-17 a beta-hydroxy-17a alpha-propinyl-D-homo-4,9(10),16-estradien-3-one, 11 beta-4-methoxyphenyl-17 beta-hydroxy-17 alpha-ethinyl-4,9(10)-estradien-3-one, 11 beta-(4-acetylphenyl)-17 beta-hydroxy-17 alpha-(prop-1-inyl)-4,9(10)estradien-3-one, 11 beta-(4-dimethylaminophenyl)-17 alpha-hydroxy-17 beta-(3-hydroxy-propyl)-13 alpha-methyl-4,9-gonadien-3-one, (Z)-11 beta-[4-(dimethylamino)phenyl]-17beta-hydroxy-17alpha-(3-hydroxy-1-propenyl)-estr-4-en-3-one-5, 11 beta-(4-acetylphenyl)-17 beta-hydroxy-17 alpha-(3-hydroxyprop-1-(Z)-enyl)-4,9(10)-estradien-3-one, 11 beta-(4-cyanophenyl)-17 beta-hydroxy-17 alpha-(3-hydroxyprop-1-(Z)-enyl)-4-androsten-3-one, 11 beta, 19-(4-(3-pyridinyl)-o-phenylene)-17 beta-hydroxy-17 alpha-(3-hydroxyprop-1-(Z)-enyl)-4-androsten-3-one, and an active metabolite of any of said progesterone antagonists or SPRMs.

2. The method of claim 1, wherein the coagulation disorder is selected from the group consisting of hemophilia, von Willebrand's disease, hepatic function impairment, thrombocytopenia, leukemia, disseminated intravascular coagulation, bone marrow aplasia and inadequate anticoagulation treatment.

3. The method of claim 1, wherein said active metabolite of asoprisnil is selected from the group consisting of J912, J956 and a combination thereof.

4. The method of claim 1, wherein said active metabolite of CDB-4124 is CDB-4453.

5. The method of claim 1, wherein said active metabolite of CDB-2914 is selected from the group consisting of CBD-3877, CDB-3963, CDB-3236, and CDB-4183, and a combination of two or more of said metabolites.

6. The method of claim 1, wherein said administration is over a period of 1 to 180 days.

7. The method of claim 1, wherein said administration is during bleeding peaks or during menstruation.

8. The method of claim 1, wherein said administration is daily, every other day, once a week or once every month.

9. The method of claim 1, wherein said administration is a one-time administration.

10. The method of claim 1, wherein said progesterone antagonist, SPRM, or active metabolite thereof is administered at a daily dose between 0.1 to 1000 mg.

11. The method of claim 10, wherein the SPRM is CDB-2914, or an active metabolite thereof, and is administered at a daily dose between 5 to 15 mg.

12. The method of claim 1, wherein said progesterone antagonist, SPRM or active metabolite thereof is administered with an oestrogen, either simultaneously or sequentially.

13. The method of claim 1, wherein said progesterone antagonist, SPRM, or active metabolite thereof is administered by vaginal, rectal, subcutaneous, intravenous, intradermal, intramuscular, intraperitoneal, intra-uterine, intranasal, transdermal, or buccal routes or via an implanted device.

14. The method of claim 1, wherein said progesterone antagonist, SPRM, or active metabolite thereof is selected from the group consisting of CDB-2914, mifepristone, CDB-4124, onapristone, org33628, 11 beta-((4-N,N-dimethylamino)-phenyl)-17 beta-hydroxy-18-methyl-17 alpha-propinyl-4,9(10)-estradien-3-one, 11 beta-((4-N,N-dimethylamino)-phenyl)-17 a beta-hydroxy-17a alpha-propinyl-D-homo-4,9(10),16-estratrien-3-one, 11 beta-4-methoxyphenyl-17 beta-hydroxy-17 alpha-ethinyl-4,9(10)-estradien-3-one, 11 beta-(4-acetylphenyl)-17 beta-hydroxy-17 alpha-(prop-1-inyl)-4,9(10)estradien-3-one, 11 beta-(4-dimethylaminophenyl)-17 alpha-hydroxy-17 beta-(3-hydroxy-propyl)-13 alpha-methyl-4,9-gonadien-3-one, (Z)-11 beta-[4-(dimethylamino)phenyl]-17beta-hydroxy-17alpha-(3-hydroxy-1-propenyl)-estr-4-en-3-one-5, 11 beta-(4-acetylphenyl)-17 beta-hydroxy-17 alpha-(3-hydroxyprop-1-(Z)-enyl)-4,9(10)-estradien-3-one, 11 beta-(4-cyanophenyl)-17 beta-hydroxy-17 alpha-(3-hydroxyprop-1-(Z)-enyl)-4-androsten-3-one, 11 beta, 19-(4-(3-pyridinyl)-o-phenylene)-17 beta-hydroxy-17 alpha-(3-hydroxyprop-1-(Z)-enyl)-4-androsten-3-one, and an active metabolite of any of said progesterone antagonists or SPRMs.

\* \* \* \* \*

UNITED STATES PATENT AND TRADEMARK OFFICE
CERTIFICATE OF CORRECTION

| | |
|---|---|
| PATENT NO. | : 8,569,274 B2 |
| APPLICATION NO. | : 12/596624 |
| DATED | : October 29, 2013 |
| INVENTOR(S) | : Fauser et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 976 days.

Signed and Sealed this
Seventh Day of April, 2015

Michelle K. Lee
*Director of the United States Patent and Trademark Office*